United States Patent

Solar et al.

[11] Patent Number: 5,947,983
[45] Date of Patent: Sep. 7, 1999

[54] TISSUE CUTTING AND STITCHING DEVICE AND METHOD

[75] Inventors: Matthew S. Solar, Cooper City; Peter K. Kratsch, Sunrise, both of Fla.

[73] Assignee: Boston Scientific Corporation, Natick, Mass.

[21] Appl. No.: 09/039,249

[22] Filed: Mar. 16, 1998

[51] Int. Cl.⁶ .......................... A61B 17/062; A61B 17/32
[52] U.S. Cl. .......................... 606/144; 606/148; 606/170; 604/22
[58] Field of Search .................................... 606/170, 171, 606/144, 148, 180; 604/22; 600/564, 565, 566, 567

[56] References Cited

U.S. PATENT DOCUMENTS

| | | | |
|---|---|---|---|
| Re. 33,258 | 7/1990 | Onik et al. ................................ | 604/22 |
| 4,557,265 | 12/1985 | Anderson ................................ | 128/340 |
| 4,598,710 | 7/1986 | Kleinberg et al. ........................ | 128/318 |
| 4,603,694 | 8/1986 | Wheeler .................................. | 128/312 |
| 4,662,869 | 5/1987 | Wright .................................... | 604/22 |
| 4,683,885 | 8/1987 | Hutterer et al. ........................... | 128/334 |
| 5,226,910 | 7/1993 | Kajiyama et al. ....................... | 606/171 |
| 5,269,791 | 12/1993 | Mayzels et al. .......................... | 606/148 |
| 5,284,472 | 2/1994 | Sussman et al. .......................... | 604/22 |
| 5,292,327 | 3/1994 | Dodd et al. ............................... | 606/148 |
| 5,336,229 | 8/1994 | Noda ....................................... | 606/144 |
| 5,395,313 | 3/1995 | Naves et al. ............................. | 604/22 |
| 5,409,013 | 4/1995 | Clement .................................. | 128/753 |
| 5,441,510 | 8/1995 | Simpson et al. ........................ | 606/159 |
| 5,458,112 | 10/1995 | Weaver ................................... | 128/753 |
| 5,505,210 | 4/1996 | Clement .................................. | 128/753 |
| 5,527,322 | 6/1996 | Clement .................................. | 606/171 |
| 5,562,685 | 10/1996 | Mollenauer et al. .................... | 606/144 |
| 5,569,277 | 10/1996 | Evans et al. ............................. | 606/159 |
| 5,582,616 | 12/1996 | Bolduc et al. ........................... | 606/143 |
| 5,643,304 | 7/1997 | Schechter et al. ....................... | 606/171 |

FOREIGN PATENT DOCUMENTS

| | | | |
|---|---|---|---|
| 541377-A1 | 5/1993 | European Pat. Off. ......... | A61B 17/32 |
| 24 53 058 | 5/1976 | Germany ......................... | A61B 10/00 |
| 2848314 | 11/1977 | Germany ......................... | A61B 17/32 |
| 4120329 | 1/1992 | Germany ......................... | A61B 17/32 |
| WO 94/28801 | 12/1994 | Germany ......................... | A61B 17/04 |
| 1454457 | 1/1989 | U.S.S.R. .......................... | A61F 17/32 |
| 2 038 640 | 12/1979 | United Kingdom ........... | A61B 17/32 |
| WO 93/14700 | 8/1993 | WIPO ............................. | A61B 10/00 |
| WO 94/16181 | 11/1994 | WIPO ............................. | A61B 17/32 |

*Primary Examiner*—Michael H. Thaler
*Attorney, Agent, or Firm*—Kenyon & Kenyon

[57] ABSTRACT

A device for cutting tissue, the device comprising a first tube having a side window; a second tube positioned within the first tube, the second tube having a side window and being movable within the first tube; a third tube positioned within the second tube, the third tube having a side window and being movable within the second tube; and a needle insertable within the second tube, the needle housing a suture. The windows in the first, second, and third tubes are alignable with each other. The invention includes methods for the cutting and suturing of tissue by using the device.

35 Claims, 9 Drawing Sheets

TISSUE CUTTING AND STITCHING DEVICE AND METHOD

FIELD OF THE INVENTION

The present invention relates to a device and method for cutting tissue, and more specifically, to grasping, cutting, and stitching tissue within a body lumen.

BACKGROUND OF THE INVENTION

When tissue surrounding a body lumen becomes cancerous or otherwise diseased, it is often necessary to remove the diseased tissue for analysis or disposal. Conventional devices and methods for such tissue removal often require open surgery to access the diseased tissue. Because open surgery is an intrusive procedure with many undesired side-effects, less invasive procedures for internal tissue removal are desired.

Recently, tissue cutters have been developed for in-situ (i.e., laparoscopic, endoscopic, etc.) tissue removal. U.S. Pat. Nos. 5,643,304 and 5,527,332, both incorporated herein by reference, describe such cutters. One limitation of these cutters, however, is that they do not provide an effective mechanism for grasping tissue before cutting. As a result, it is often difficult to accurately remove localized diseased tissue without also removing a substantial amount of the surrounding tissue. Moreover, conventional cutters do not provide a means for suturing the tissue from which the diseased tissue has been removed. It is therefore not possible to use such devices alone for the removal of the full-wall thickness of a body lumen without leakage from the lumen (of blood, feces, etc.).

SUMMARY OF THE INVENTION

The present invention is directed to a device and method for cutting tissue from any body lumen such as, for example, veins, arteries, the stomach, intestines, esophagus and bowels.

In one aspect, the present invention provides a device for cutting tissue comprising a plurality of tubes insertable within each other. Each of the tubes has a window therein to facilitate the grasping and cutting of tissue within a body lumen. The device preferably includes a needle for suturing the lumen after cutting and removal of tissue therefrom.

In one embodiment, the device of the present invention includes first, second and third tubes, each having a side window therein. The first tube extends from a proximal portion to a distal portion and has a side window in the distal portion. In an operative position, the distal portion of the first tube is located within a body lumen adjacent to the tissue to be cut. The second tube extends from a proximal portion to a distal portion, wherein the distal portion is moveably mounted within the distal portion of the first tube. The second tube has a second side window which, when the first and second tubes are in an alignment with respect to one another, faces the first side window so that an interior of the second tube is open to an exterior of the first tube. The third tube extends from a proximal portion to a distal portion, wherein the distal portion is moveably mounted within the distal portion of the second tube. The third tube has a third side window, wherein the third window is alignable with the first and second windows.

In another aspect, the present invention provides a method for cutting tissue from a body lumen, comprising the steps of providing the device as described above, wherein the third tube is a vacuum tube; inserting the device into the body lumen so that the first window is positioned adjacent to a portion of tissue to be cut; aligning the windows in each of the first, second and vacuum tubes to form an opening in the device which extends from an exterior of the first tube to an interior of the vacuum tube; sucking a portion of tissue into the opening; moving the second tube with respect to the first tube to reduce the size of the opening and to grasp the portion of tissue to be cut; and moving the third tube with respect to the first and second tubes to cut the grasped portion of tissue.

In yet another aspect, the present invention provides a method for cutting a portion of tissue protruding from a body lumen, comprising the steps of inserting a device as described above into the body lumen; inserting the device into the body lumen so that the first window is positioned adjacent to the portion of tissue to be cut; aligning the windows in the first and second tubes to form an opening in the device extending from an exterior of the first tube to an interior of the second tube; positioning the opening over the protrusion; moving the second tube with respect to the first tube to grasp the body lumen wall adjacent to the protrusion; positioning the window in the third tube over the grasped protrusion; and moving the third tube with respect to the first and second tubes to cut the protrusion from the body lumen.

In yet another aspect, the present invention provides a method for cutting a portion of tissue from a body lumen using a tissue grasper. In this aspect, the device includes a tissue grasper within the third tube. The method comprises the steps of inserting the device into the body lumen so that the first window is positioned adjacent to a portion of tissue to be cut; aligning the first, second and third windows to form an opening in the device extending from an exterior of the first tube to an interior of the third tube; extending the tissue grasper through the opening; grasping the portion of tissue to be cut with the tissue grasper; pulling the portion of tissue to be cut into the opening; moving the second tube with respect to the first tube to reduce the size of the opening and grasp the portion of tissue to be cut; and moving the third tube with respect to the first and second tubes to cut the grasped tissue.

DETAILED DESCRIPTION

The present invention provides for the removal of tissue from a body lumen without resorting to open surgery and allows for the identification of tissue desired for removal from a body lumen. As accurate, localized cutting of that tissue and preferably, in-situ suturing of the remaining tissue is possible, the full thickness of a body lumen wall can be extracted without resulting in excessive bleeding or leakage from the lumen.

Figure 1A:
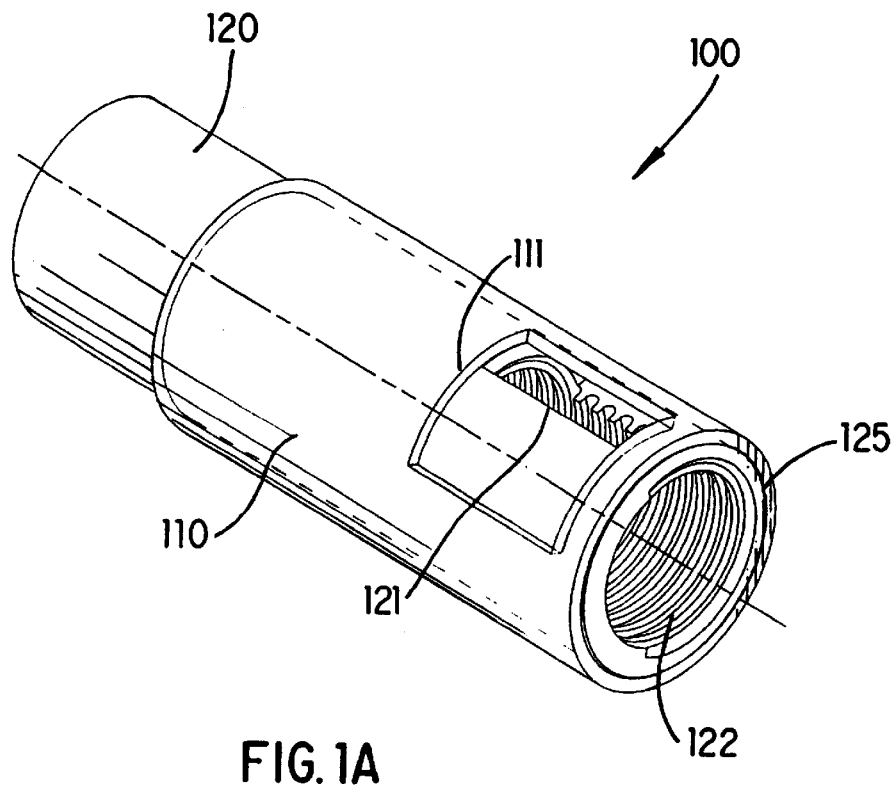
FIG. 1A illustrates a first portion of a device according to the present invention.
Figure 1B:
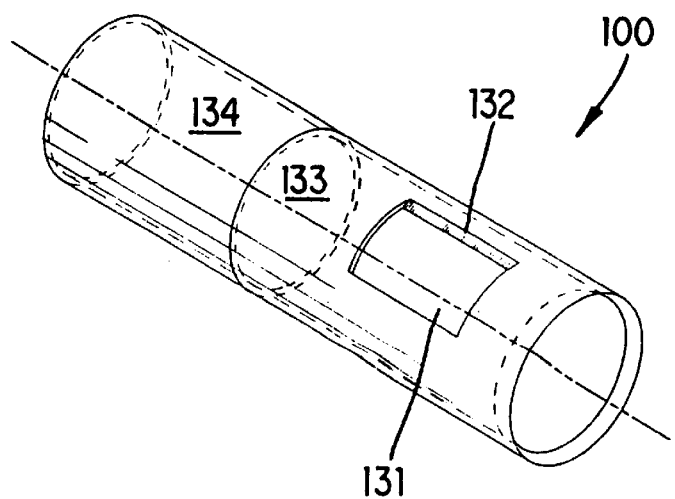
FIG. 1B illustrates a second portion of the device of FIG. 1A.
Figure 1C:
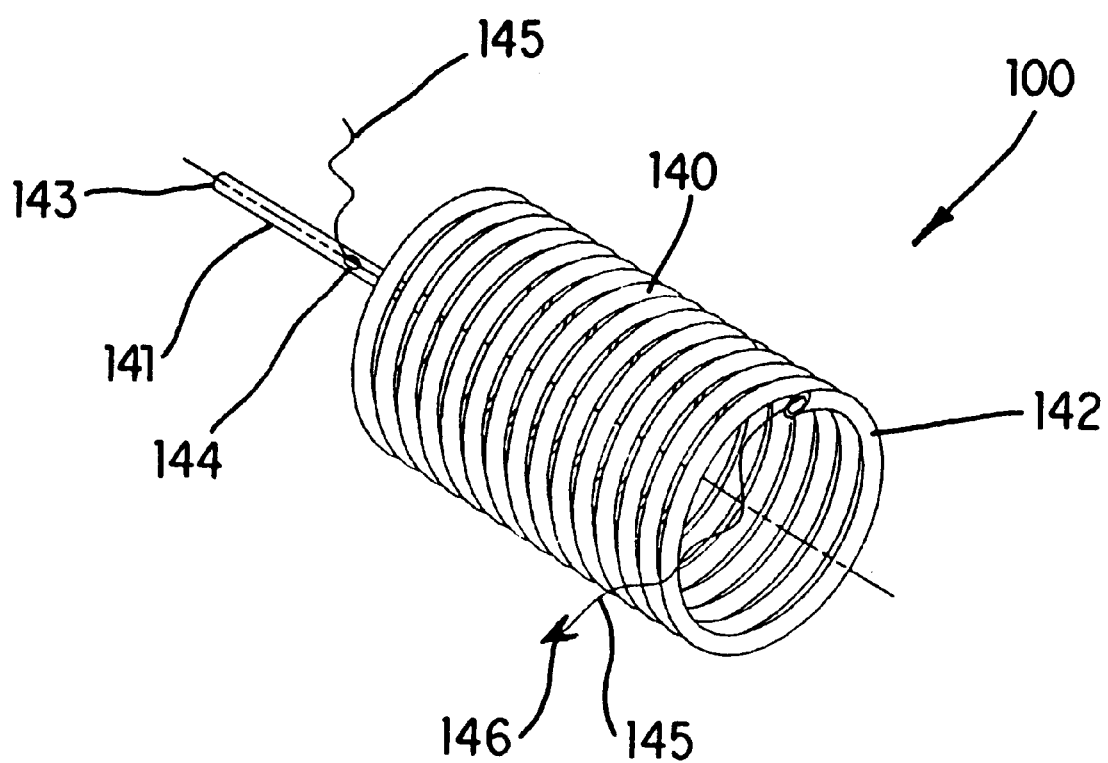
FIG. 1C illustrates a third portion of the device of FIG. 1A.

FIGS. 1A–1C show a device according to the present invention. As shown in FIG. 1A, a grasper portion of a device 100 includes a first tube 110 and a second tube 120, wherein the second tube 120 is movable within the first tube 110. The first and second tubes 110, 120 include windows 111 and 121, respectively, which may be aligned with each other as shown in FIG. 1A by moving the second tube 120 axially relative to the first tube 110 or by rotating the first and second tubes 110, 120 relative to one another. A third tube 130, as shown in FIG. 1B, is moveably mountable within the second tube 120 and includes a third window 131.

The third window 131 preferably includes at least one cutting edge 132 which may be formed as part of the third window 131 by machining, for example. The cutting edge 132 is preferably positioned so that, when the windows 111, 121 and 131 are aligned to expose the interior of the tube 130 to the environment outside the device 100, the cutting edge 132 extends perpendicular to a direction of relative movement between the third tube 130 and the first and second tubes 110, 120. That is, the cutting edge 132 is positioned so that when a cutting movement is performed, the cutting edge 132 moves from a first side of the opening 121, across opening 121, to a second side thereof. For example, if the third tube 130 is rotatable relative to the second tube 120, the cutting edge 132 would preferably extend parallel to the axis of the tubes 110, 120 and 130. However, if the tubes 110, 120 and 130 are moveable axially relative to one another, the cutting edge 132 would preferably extend circumferentially around a portion of the third tube 130.

The windows 111, 121 and 131 are of any suitable shape such as, for example, rectangular, circular, or oval. Moreover, the windows 111, 121 and 131 may extend in a longitudinal or circumferential direction, the choice of which depends on the shape of the tissue to be removed and the shape and depth of the cut to be made.

Figure 2A:
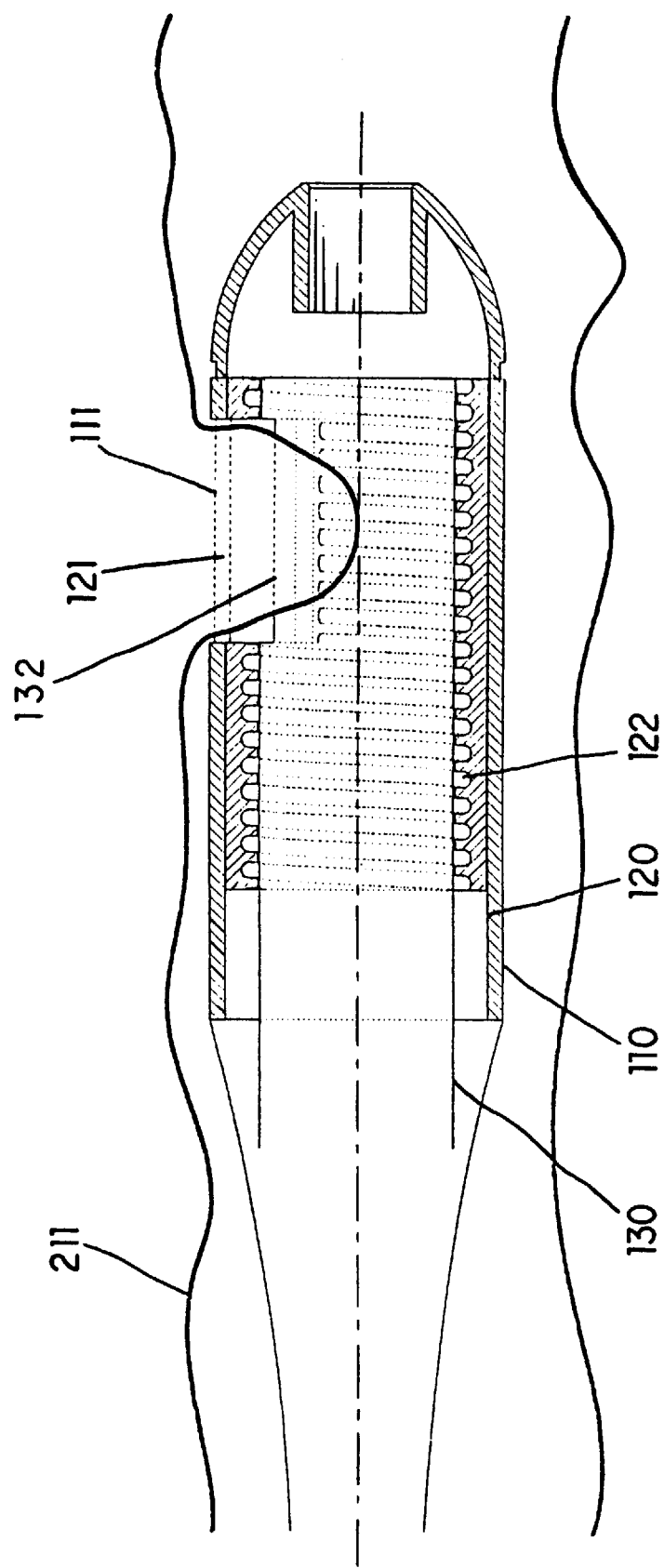
FIGS. 2A–2E illustrate a method for cutting and removing tissue from a body lumen wall, in accordance with the present invention.
Figure 2B:
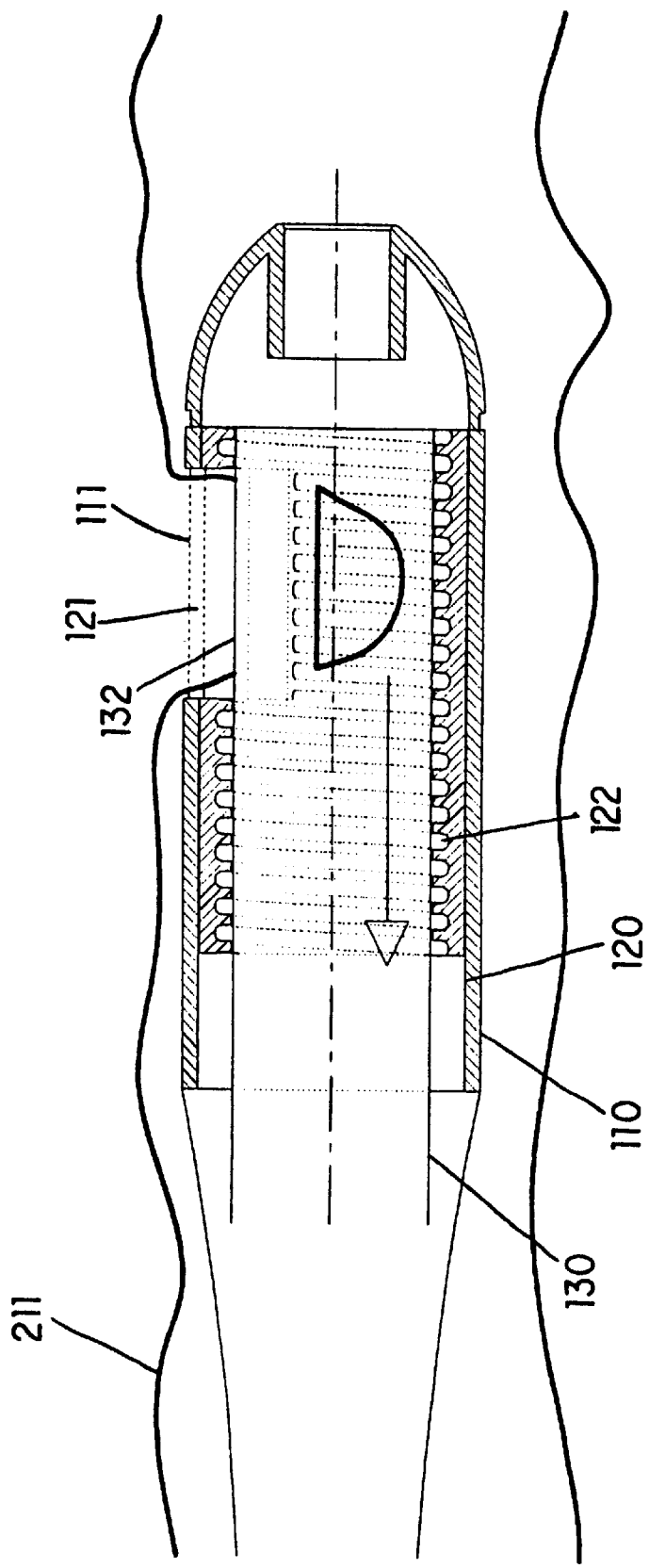

The device 100 is used, for example, to cut tissue from the side wall of a body lumen. In this embodiment, third tube 130 is a vacuum tube such that when device 100 is inserted into body lumen 211 and the windows in the first, second and vacuum tubes are aligned, tissue from lumen 211 is sucked into the vacuum tube as shown in FIG. 2A. Second tube 120 is thereafter moved with respect to first tube 110 to pinch the tissue against the edges of the windows 111 and 121 to grasp the tissue that has been sucked into vacuum tube 130. Vacuum tube 130 is then moved with respect to the second tube 120, thereby cutting and removing the grasped tissue with cutting edge 132, as shown in FIG. 2B. This aspect of the present invention is particularly well-adapted to the removal of full-wall thickness sections of a body lumen.

Figure 2C:
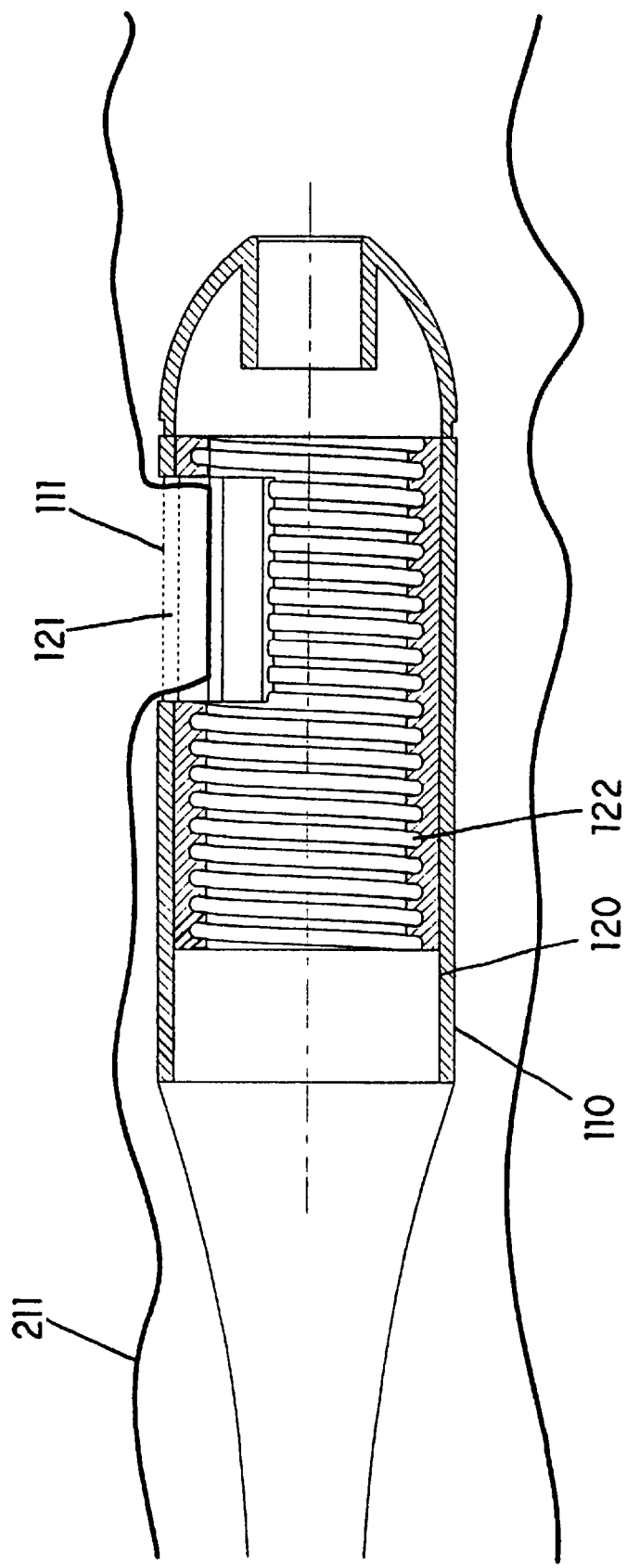
Figure 2D:
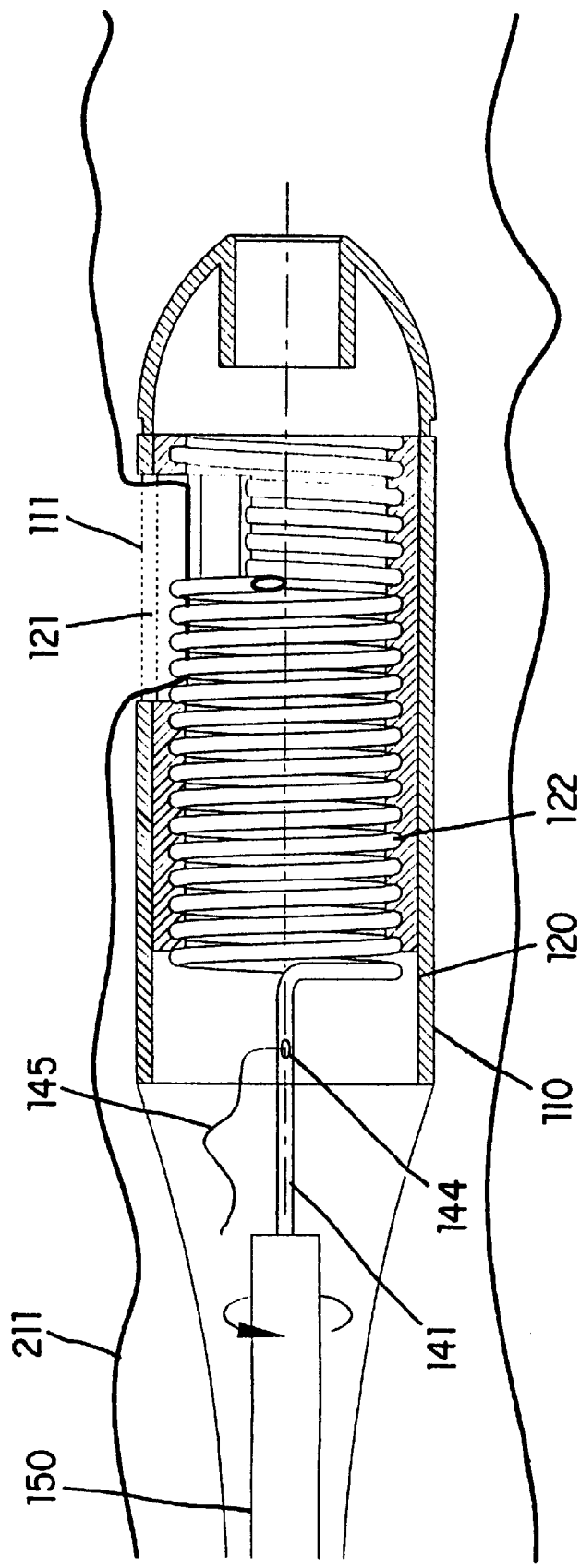

To facilitate the immediate suturing of the cut edges of the lumen wall 211 after, for example, the full-wall thickness cutting and removal of diseased tissue, the third tube 130 is removed from the second tube 120 (FIG. 2C) and a needle 140 is inserted into the second tube 120 (FIG. 2D). Alternatively, the third tube 130 remains within the second tube 120 while the needle 140 advances within the second tube 120. The needle 140 is inserted into the second tube 120 before the lumen wall is released by the first and second tubes 110 and 120, respectively. As shown in FIG. 1C, the needle 140 has proximal and distal ends 141 and 142, respectively, and a central bore 143, which houses the suture 145. The distal end 142 preferably includes a sharpened tip suitable for piercing tissue. The needle 140, which optionally includes a side opening 144 for the introduction of the suture 145 into the central bore 143, is mounted on a push bar 150 or the like for positioning and rotating the needle 140 within the second tube 120.

In use, the needle 140 is inserted through the grasped portion of body lumen wall by any suitable means. For example, it is preferred that the needle 140 be in the shape of a helix as shown in FIG. 1C. In this case, the second tube 120 preferably has a helical groove 122 in its inner surface adapted to receive the needle 140 such that the needle 140 is advanced through the second tube 120 and the grasped portion of body lumen side wall 211 by placing the needle 140 in the groove 122 and rotating the needle 140 to advance the needle 140 towards the distal end 125 of the second tube 120, as shown in FIG. 2D. The needle 140 may, for example, be manipulated by a flexible push bar 150, a distal end of which is attached to the needle 140 while a proximal end of the push bar 150 is coupled to an actuator (not shown) accessible to the user.

Figure 2E:
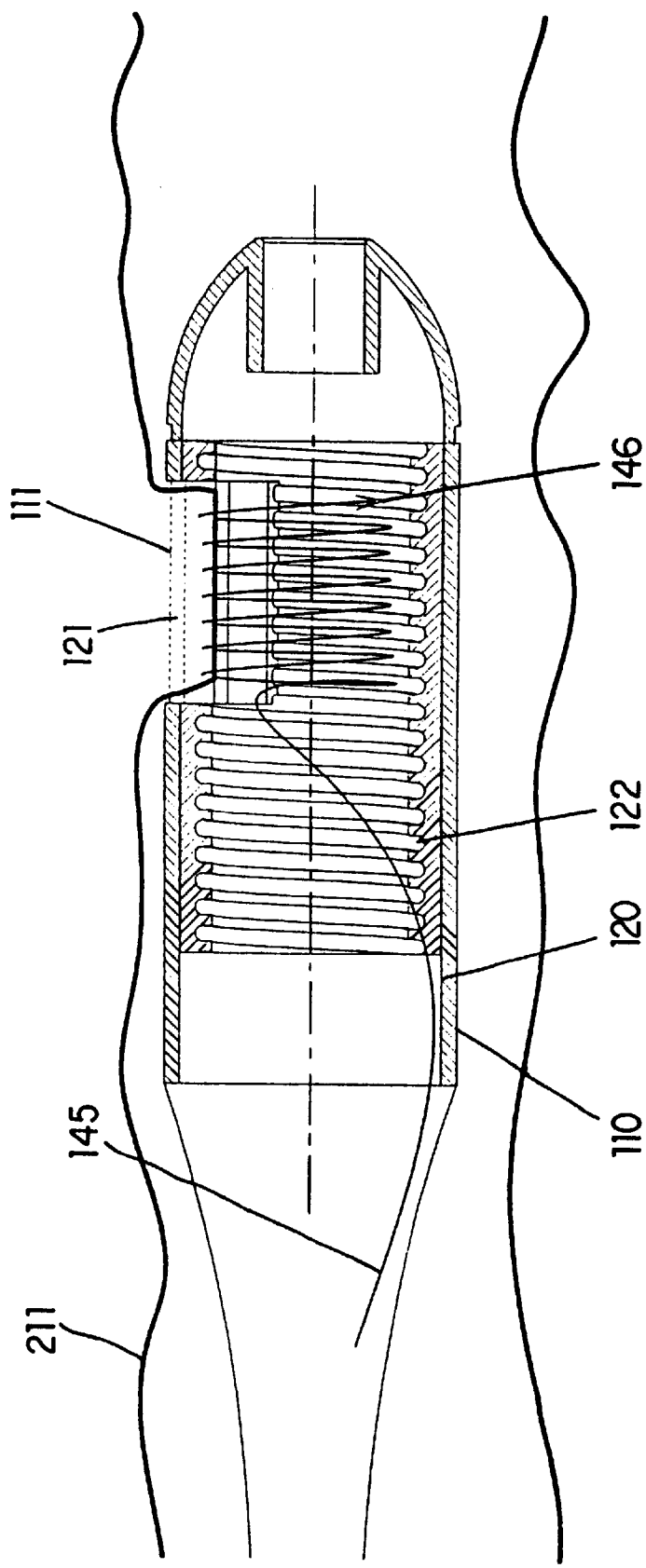

Once the needle 140 has been pushed through the grasped portion of lumen wall 211, it is withdrawn while leaving the suture 145 in place, as shown in FIG. 2E. If the needle 140 is in the shape of a helix, its withdrawal is achieved, for example, by rotating the needle 140 in a direction opposite that by which it was inserted so that the needle 140 moves away from the distal end 125 of the second tube 120. As shown in FIG. 1C, the suture 145 preferably includes an anchor portion 146 which may comprise an elastic material such as a polymeric material, a suitable biocompatible suture material, or a metallic material such as stainless steel or nitinol, for example. When the suture 145 is maintained within the needle 140, the anchor portion 146 is compressed by the outer wall of the central bore 143. When the suture 145 is pushed out of the needle 140, however, the anchor portion 146 expands under its spring bias into a desired shape selected to anchor the suture 145 against the grasped tissue. For example, the anchor portion 146 has an arrowhead configuration as shown in FIG. 1C. Alternatively, rather than being compressed within the needle 140, the anchor portion 146 may be held against the distal end 142 of needle 140 to form a sharpened tip suitable for piercing tissue. Before the needle 140 is withdrawn from the grasped portion of body lumen 211, the anchor portion 146 is extended away from the distal end 142 of the needle 140 by any suitable means, such as by applying pressure to the suture 145.

Figure 2F:
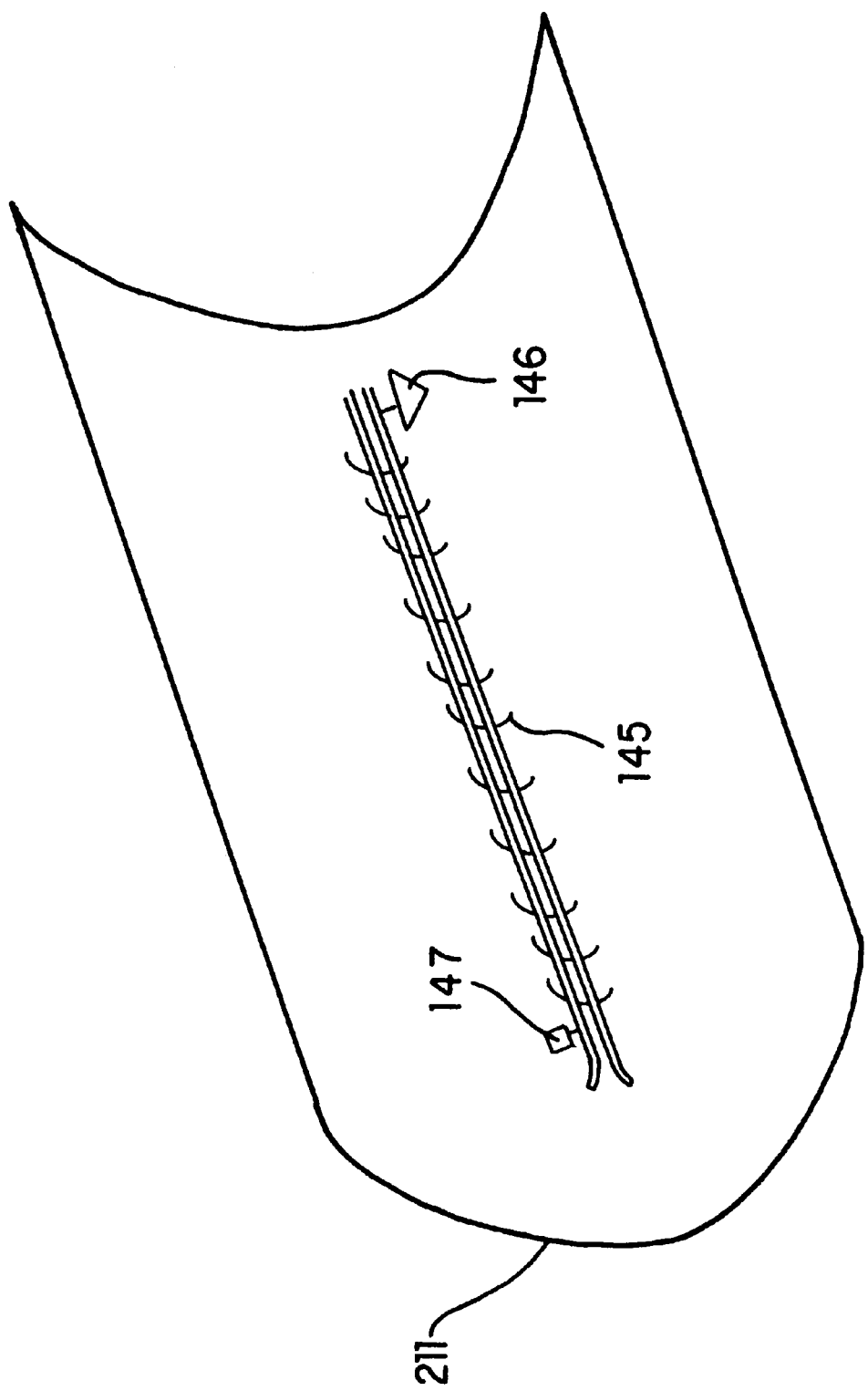
FIG. 2F illustrates a portion of a body lumen that has been cut and sutured.

The suture 145 appears as shown in FIG. 2E after the needle 140 is withdrawn. The suture 145 is thereafter tightened by any suitable method. For example, a grasper as known in the art may be inserted into the second tube 120 to grasp and tighten the suture 145. The tightened suture 145 is secured by any suitable method, such as by tying off its free end or by crimping a suture termination element 147 onto its free end. FIG. 2F shows such a tightened suture over a cut portion of a body lumen wall 211. After the suture 145 is secured, the wall of body lumen 120 is released from the first and second tubes, 110 and 120, respectively, which are thereafter withdrawn from the body lumen.

The device 100 is also used, for example, to cut a protrusion extending from the side of a body lumen using the method illustrated in FIGS. 2A–2F. It is not necessary, however, that the third tube 130 be a vacuum tube for this purpose so long as the protrusion extends far enough away from the body lumen side wall 211 to facilitate insertion into third tube 130 for cutting.

The tubes 110, 120 and 130 are catheters, for example, that extend from outside of the body to the location within a body lumen from which tissue is to be removed, thus allowing for the easy manipulation of each of the tubes by a physician. The manipulation of the tubes 110, 120 and 130 is also suitable to laparoscopic techniques. As such, these tubes are made of a flexible material, as is known in the art. A portion 133 of the third tube 130, however, is preferably a rigid material such as stainless steel to allow the cutting edge 132 to be an integral part of the third tube 130. In this case, the rigid portion 133 is attached to a flexible portion 134 of the third tube 130 by any suitable means, such as by an interlocking joint. Alternatively, the third tube 130 is made of a single, flexible material to which the cutting edge 132 is added. The tubes 110, 120 and 130 are of any suitable size that is limited only by the inner diameter of body lumen into which the tubes are inserted.

The tubes 110, 120 and 130 are introduced into the body by any suitable means. It is preferred, however, that the device of the present invention be inserted into the body in association with an endoscope (e.g., within a working channel of an endoscope or over the exterior surface of an endoscope), which allows for the in-situ identification of diseased tissue. Once the endoscope is positioned to a target location within a body lumen, the device 100 is extended from the endoscope working channel to grasp, cut and remove diseased tissue. Alternatively, the device 100 is inserted into a body lumen without the use of an endoscope. In this latter case, fluoroscopic or similar techniques may be used to view and position the device 100 during use.

Figure 3:
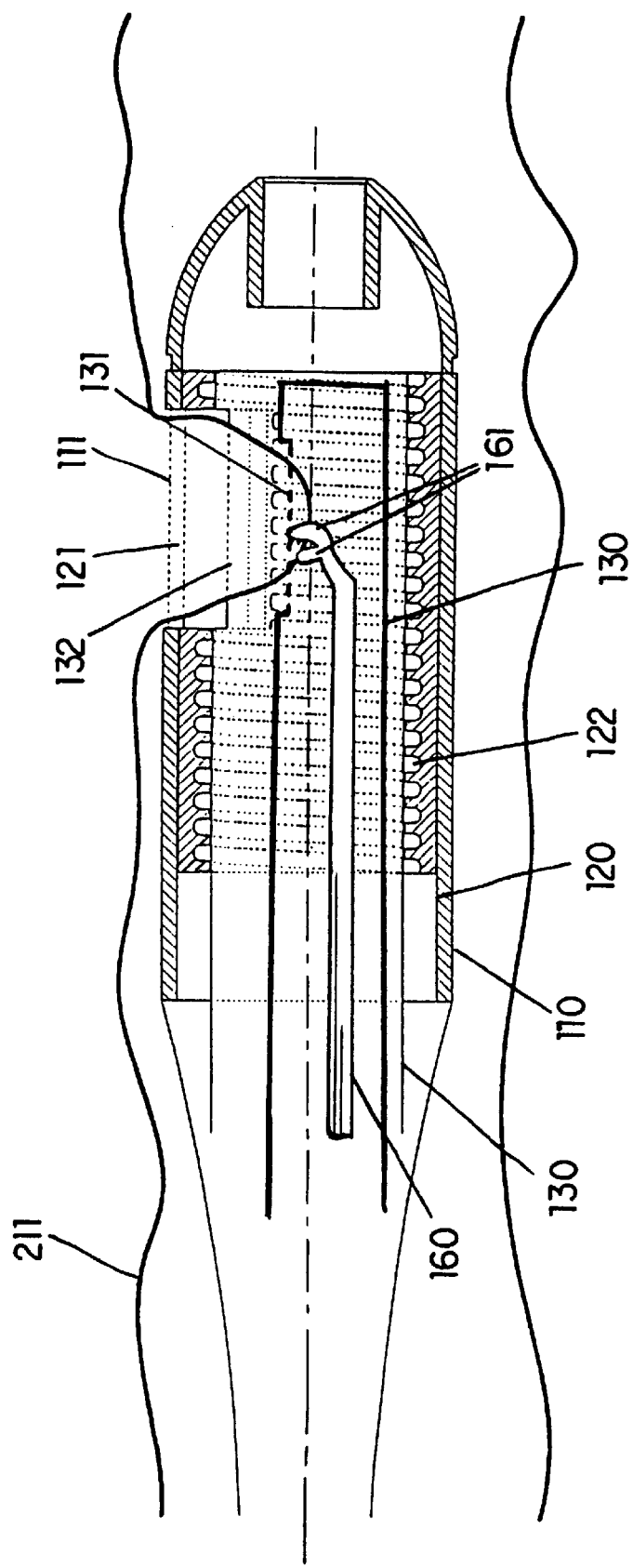
FIG. 3 illustrates an embodiment of the present invention that includes a tissue grasper.

Any embodiment of the present invention optionally includes a tissue grasper 160 within the third tube 130, as shown in FIG. 3. As is known in the art, the tissue grasper grabs tissue with, for example, a pair of jaws, 161. Use of the tissue grasper 160 is preferred where the third tube 130 is not a vacuum tube. In this situation, the cutting and stitching of tissue or protrusions from body lumen walls occurs by the methods as herein described and illustration, except that the grasped tissue is pulled into the third tube by the tissue grasper 160 rather than by the action of vacuum.

The present invention provides a device and method for the minimally-invasive grasping, cutting and removal of diseased tissue from within a body lumen. Those with skill in the art may recognize various modifications to the embodiments of the invention described and illustrated herein. Such modifications are meant to be covered by the spirit and scope of the appended claims.

We claim:

1. A device for cutting tissue within a body lumen, said device comprising:
    a first tube extending from a proximal portion to a distal portion, wherein, in an operative position, the distal portion is located within the body lumen adjacent to the tissue to be cut; the first tube having a side window in the distal portion thereof;
    a second tube extending from a proximal portion to a distal portion, wherein the distal portion is moveably mounted within the distal portion of the first tube, said second tube having a second side window which, when the first and second tubes are in an alignment with respect to one another, faces the first side window so that an interior of the second tube is open to an exterior of the first tube; and
    a third tube extending from a proximal portion to a distal portion, wherein the distal portion is moveably mounted within the distal portion of the second tube, said third tube having a third side window, wherein said third window is alignable with said first and second windows.

2. The device of claim 1, wherein said third window has at least one cutting edge.

3. The device of claim 1, wherein said third tube is a vacuum tube through which negative pressure may be applied to draw tissue into the first, second and third windows.

4. The device of claim 1, further comprising a tissue grasper within said third tube, said tissue grasper for grasping and drawing tissue into the first, second and third windows.

5. The device of claim 1, further comprising a needle insertable within said second tube, said needle housing a suture.

6. The device of claim 5, wherein said needle is substantially helical.

7. The device of claim 6, wherein said second tube has a substantially helical groove in an inner surface thereof, said helical groove being adapted to receive said needle.

8. The device of claim 5, wherein said suture comprises an anchor portion, which when penetrated through a portion of tissue, resists removal therefrom and thus maintains the suture in a desired position.

9. The device of claim 8, wherein said anchor portion comprises an elastic material.

10. The device of claim 9, wherein said elastic material is selected from the group consisting of a polymeric material, stainless steel and nitinol.

11. The device of claim 8, wherein said anchor portion has a pointed tip.

12. The device of claim 8, wherein during insertion of the needle through the tissue, the anchor member is maintained in a storage position within the needle and, when released from the needle, the anchor member expands to an anchor position.

13. The device of claim 1, wherein said first, second and third windows are elongated in a longitudinal direction of said first, second and third tubes, respectively.

14. The device of claim 1, wherein said first, second and third windows are elongated in the circumferential direction of said first, second and third tubes, respectively.

15. A method for cutting tissue from a body lumen, said method comprising the steps of:
    providing a device comprising:
        a first tube extending from a proximal portion to a distal portion, wherein, in an operative position, the distal portion is located within the body lumen adjacent to the tissue to be cut; the first tube having a side window in the distal portion thereof;
        a second tube extending from a proximal portion to a distal portion, wherein the distal portion is moveably mounted within the distal portion of the first tube, said second tube having a second side window which, when the first and second tubes are in an alignment with respect to one another, faces the first side window so that an interior of the second tube is open to an exterior of the first tube; and
        a vacuum tube extending from a proximal portion to a distal portion, wherein the distal portion is moveably mounted within the distal portion of the second tube, said vacuum tube having a third side window, wherein said third window is alignable with said first and second windows;
    inserting said device into the body lumen so that the first window is positioned adjacent to a portion of tissue to be cut;
    aligning said first, second and third windows to form an opening in said device extending from an exterior of said first tube to an interior of said vacuum tube;
    sucking the portion of tissue to be cut into said opening;
    moving said second tube with respect to said first tube to reduce the size of said opening and grasp the portion of tissue to be cut; and moving said vacuum tube with respect to said first and second tubes to cut the grasped tissue.

16. The method of claim 15, wherein said step of inserting said device into the body lumen occurs via a natural body orifice.

17. The method of claim 15, further comprising the steps of:
    inserting a needle into said second tube, said needle housing a suture;
    pushing said needle through said grasped tissue;
    withdrawing said needle from the grasped tissue, said step of withdrawing leaving said suture through the grasped tissue; and
    tightening said suture to seal a wound resulting from the cutting of the grasped tissue.

18. The method of claim 17, wherein said vacuum tube is removed from said second tube before said needle is inserted into said second tube.

19. The method of claim 17, wherein:
    said needle is substantially helical;
    said second tube has a substantially helical groove formed in an inner surface thereof, said helical groove being adapted to receive said needle;
    said step of pushing said needle through the grasped tissue includes the steps of:
        placing said needle in said groove, and rotating said needle in a first direction about its longitudinal axis to advance the needle towards the grasped tissue and to push the needle through the grasped tissue; and
    said step of withdrawing said needle from the grasped tissue includes the step of rotating said needle in a second direction about a longitudinal axis thereof, said second direction being opposite said first direction.

20. The method of claim 15, wherein said window in said vacuum tube has at least one cutting edge.

21. The method of claim 15, wherein said step of moving of said second tube includes the step of rotating said second tube relative to said first tube.

22. The method of claim 15, wherein said step of moving said second tube includes the step of moving said second tube relative to the first tube along a longitudinal axis of the second tube.

23. The method of claim 15, wherein said step of moving said vacuum tube includes the step of rotating said vacuum tube relative to the second tube.

24. The method of claim 15, wherein said step of moving said vacuum tube includes the step of moving said vacuum tube relative to the second tube along a longitudinal axis of the vacuum tube.

25. A method for cutting a portion of tissue protruding from a body lumen, said method comprising the steps of:
    providing a device comprising:
        a first tube extending from a proximal portion to a distal portion, wherein, in an operative position, the distal portion is located within the body lumen adjacent to the tissue to be cut; the first tube having a side window in the distal portion thereof;
        a second tube extending from a proximal portion to a distal portion, wherein the distal portion is moveably mounted within the distal portion of the first tube, said second tube having a second side window which, when the first and second tubes are in an alignment with respect to one another, faces the first side window so that an interior of the second tube is open to an exterior of the first tube; and
        a third tube extending from a proximal portion to a distal portion, wherein the distal portion is moveably mounted within the distal portion of the second tube, said third tube having a third side window, wherein said third window is alignable with said first and second windows;
    inserting said device into the body lumen so that the first window is positioned adjacent to a portion of tissue to be cut;
    aligning said first and second windows to form an opening in said device extending from an exterior of said first tube to an interior of said second tube;
    positioning said opening over the portion of tissue to be cut so that the portion of tissue extends into the opening;
    moving said second tube with respect to said first tube to grasp the tissue received within the opening;
    positioning said window in said third tube over the grasped tissue; and
    moving said third tube with respect to said first and second tubes to cut the grasped tissue from the body lumen.

26. The method of claim 25, wherein said step of inserting said device into the body lumen occurs via a natural body orifice.

27. The method of claim 25, further comprising the steps of:
    inserting a needle into said second tube, said needle housing a suture;
    pushing said needle through said grasped tissue;
    withdrawing said needle from the grasped tissue, said step of withdrawing leaving said suture through the grasped tissue; and
    tightening said suture to seal a wound resulting from the cutting of the grasped tissue.

28. The method of claim 25, wherein said third tube is removed from said second tube before said needle is inserted into said second tube.

29. The method of claim 25, wherein:
    said needle substantially helical;
    said second tube has a substantially helical groove formed in an inner surface thereof, said helical groove being adapted to receive said needle;
    said step of pushing said needle through the grasped tissue includes the steps of:
        placing said needle in said groove, and rotating said needle in a first direction about its longitudinal axis to advance the needle towards the grasped tissue and to push the needle through the grasped tissue; and
    said step of withdrawing said needle from the grasped tissue includes the step of rotating said needle in a second direction about a longitudinal axis thereof, said second direction being opposite said first direction.

30. The method of claim 25, wherein said window in said third tube has at least one cutting edge.

31. The method of claim 25, wherein said step of moving of said second tube includes the step of rotating said second tube relative to said first tube.

32. The method of claim 25, wherein said step of moving said second tube includes the step of moving said second tube relative to the first tube along a longitudinal axis of the second tube.

33. The method of claim 25, wherein said step of moving said third tube includes the step of rotating said third tube relative to the second tube.

34. The method of claim 25, wherein said step of moving said third tube includes the step of moving said third tube relative to the second tube along a longitudinal axis of the third tube.

35. A method for cutting tissue from a body lumen, said method comprising the steps of:

provideing a device comprising:

a first tube extending from a proximal portion to a distal portion, wherein, in an operative position, the distal portion is located within the body lumen adjacent to the tissue to be cut; the first tube having a side window in the distal portion thereof;

a second tube extending from a proximal portion to a distal portion, wherein the distal portion is moveably mounted within the distal portion of the first tube, said second tube having a second side window which, when the first and second tubes are in an alignment with respect to one another, faces the first side window so that an interior of the second tube is open to an exterior of the first tube; and a third tube extending from a proximal portion to a distal portion, wherein the distal portion is moveably mounted within the distal portion of the second tube, said third tube having a third side window, wherein said third window is alignable with said first and second windows;

a tissue grasper extending from a proximal portion to a distal portion, wherein the distal portion is moveably mounted within said third tube, inserting said device into the body lumen so that the first window is positioned adjacent to a portion of tissue to be cut;

aligning said first, second and third windows to form an opening in said device extending from an exterior of said first tube to an interior of said third tube;

extending said tissue grasper through said opening;

grasping the portion of tissue to be cut with said tissue grasper;

pulling the portion of tissue to be cut into said opening;

moving said second tube with respect to said first tube to reduce the size of said opening and grasp the portion of tissue to be cut; and moving said third tube with respect to said first and second tubes to cut the grasped tissue.

* * * * *